United States Patent [19]

Durkan

[11] Patent Number: 4,506,666

[45] Date of Patent: Mar. 26, 1985

[54] METHOD AND APPARATUS FOR RECTIFYING OBSTRUCTIVE APNEA

[75] Inventor: Gerald Durkan, Altoona, Pa.

[73] Assignee: Kircaldie, Randall and McNab, Wethersfield, Conn.

[21] Appl. No.: 446,543

[22] Filed: Dec. 3, 1982

[51] Int. Cl.³ ............................................. A61M 16/00
[52] U.S. Cl. .......................... 128/204.23; 128/204.24; 128/419 G
[58] Field of Search ................ 128/28, 204.21, 204.22, 128/204.23, 204.24, 204.25, 204.26, 204.28, 205.24, 205.25, 419 G, 205.14, 205.15, 205.16, 205.18, 716, 721, 724

[56] References Cited

U.S. PATENT DOCUMENTS

| | | | |
|---|---|---|---|
| 2,532,788 | 12/1950 | Sarnoff | 128/28 |
| 3,357,428 | 12/1967 | Carlson | 128/204.26 |
| 3,547,106 | 12/1970 | Bornmann | 128/721 |
| 3,802,417 | 4/1974 | Lang | 128/716 |
| 3,942,513 | 3/1976 | Frank | 128/28 |
| 3,976,064 | 8/1976 | Wood et al. | 128/204.28 |
| 4,054,134 | 10/1977 | Kritzer . | |
| 4,062,358 | 12/1977 | Kritzer . | |
| 4,121,579 | 10/1978 | Bird | 128/204.25 |
| 4,155,356 | 5/1979 | Venegas . | |
| 4,226,233 | 10/1980 | Kritzer . | |

OTHER PUBLICATIONS

Sullivan et al., "Reversal of Obstructive Sleep Apnoea by Continuous Positive Airway Pressure Applied through the Nares", *The Lancet*, Apr. 18, 1981, pp. 862–865.

*Primary Examiner*—Henry J. Recla
*Attorney, Agent, or Firm*—Griffin, Branigan & Butler

[57] ABSTRACT

Upon the detection of an appropriate apnea event, respirating gas supply apparatus according to various embodiments supply stimulus to the upper airway passages of an in vivo respiratory system in an effort to dislodge any occlusion or obstruction in the upper airway passages. In one embodiment the stimulus applied is a high pressure pulse of gas. In another embodiment an electrical signal is applied to an electromyographic electrode (270) positioned in proximity to a nerve controlling a muscle or organ which may obstruct the upper airway passage.

21 Claims, 14 Drawing Figures

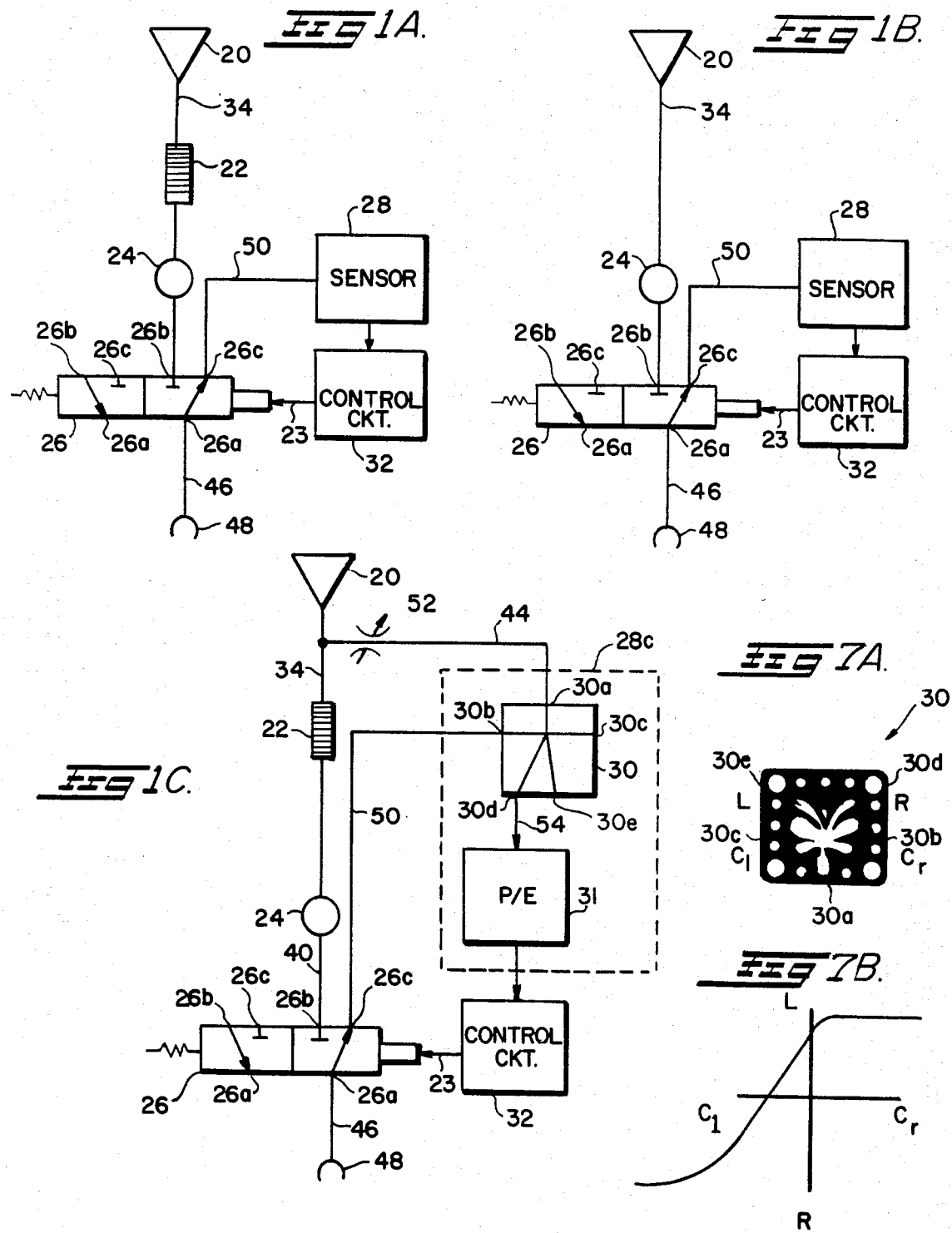

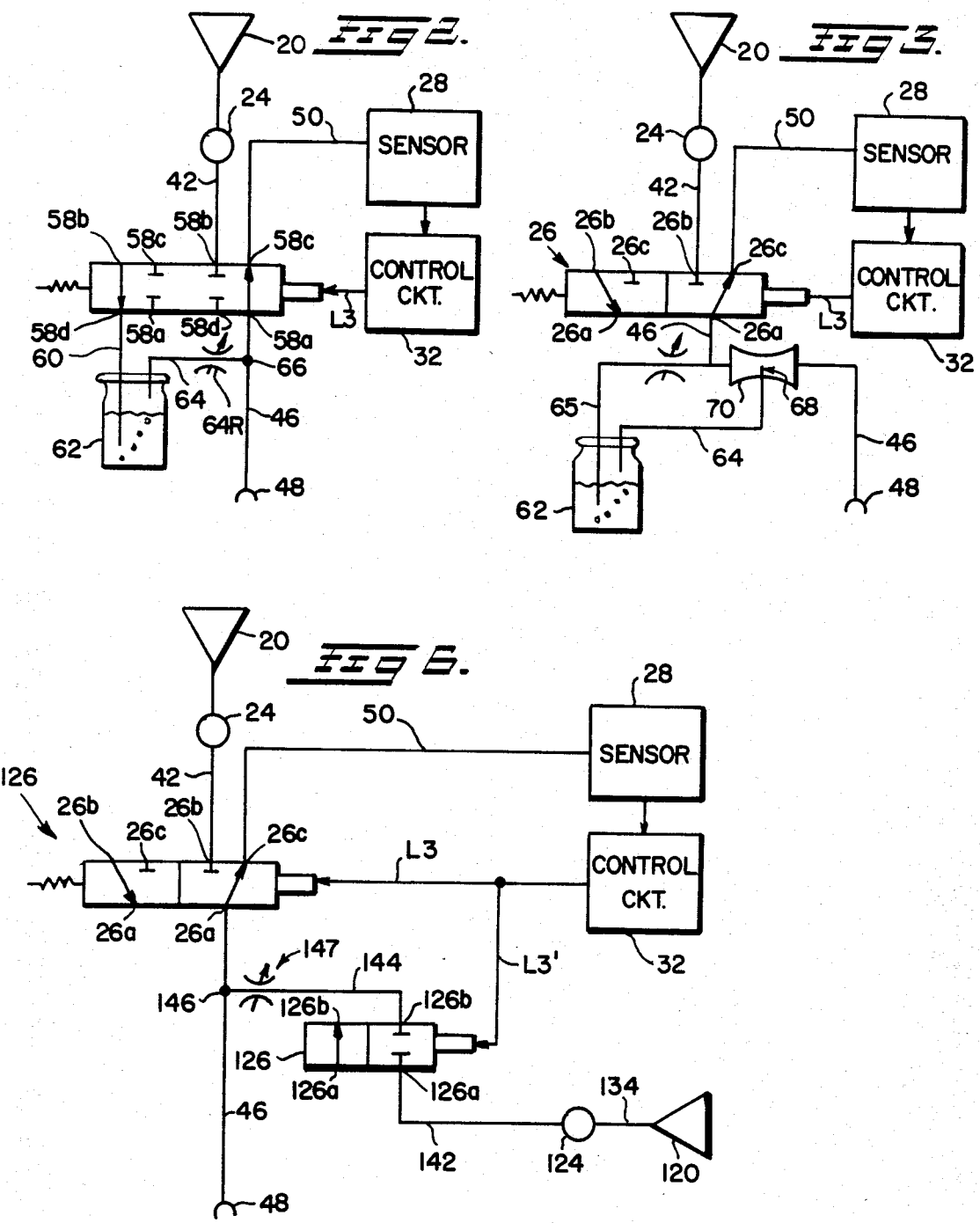

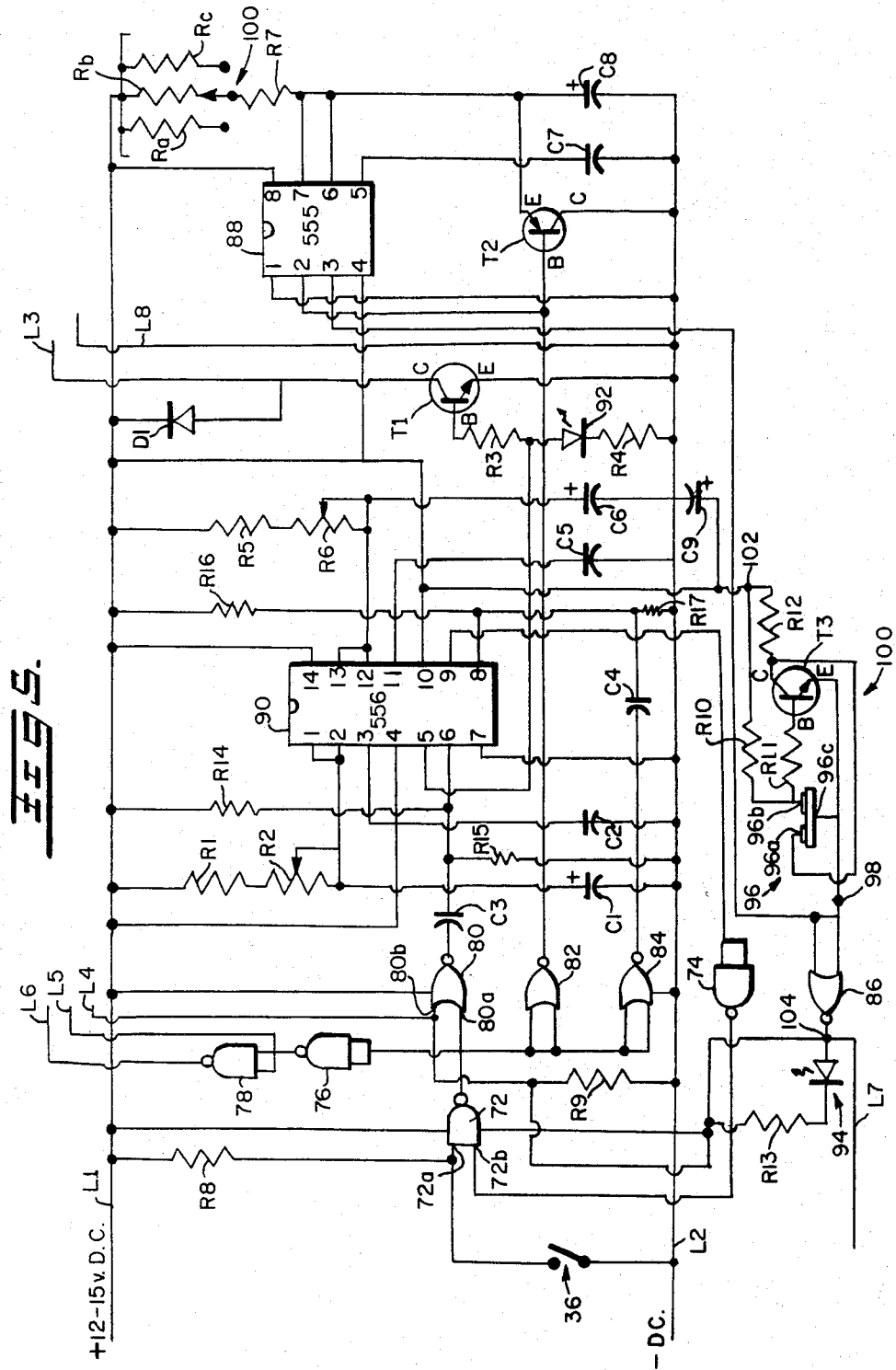

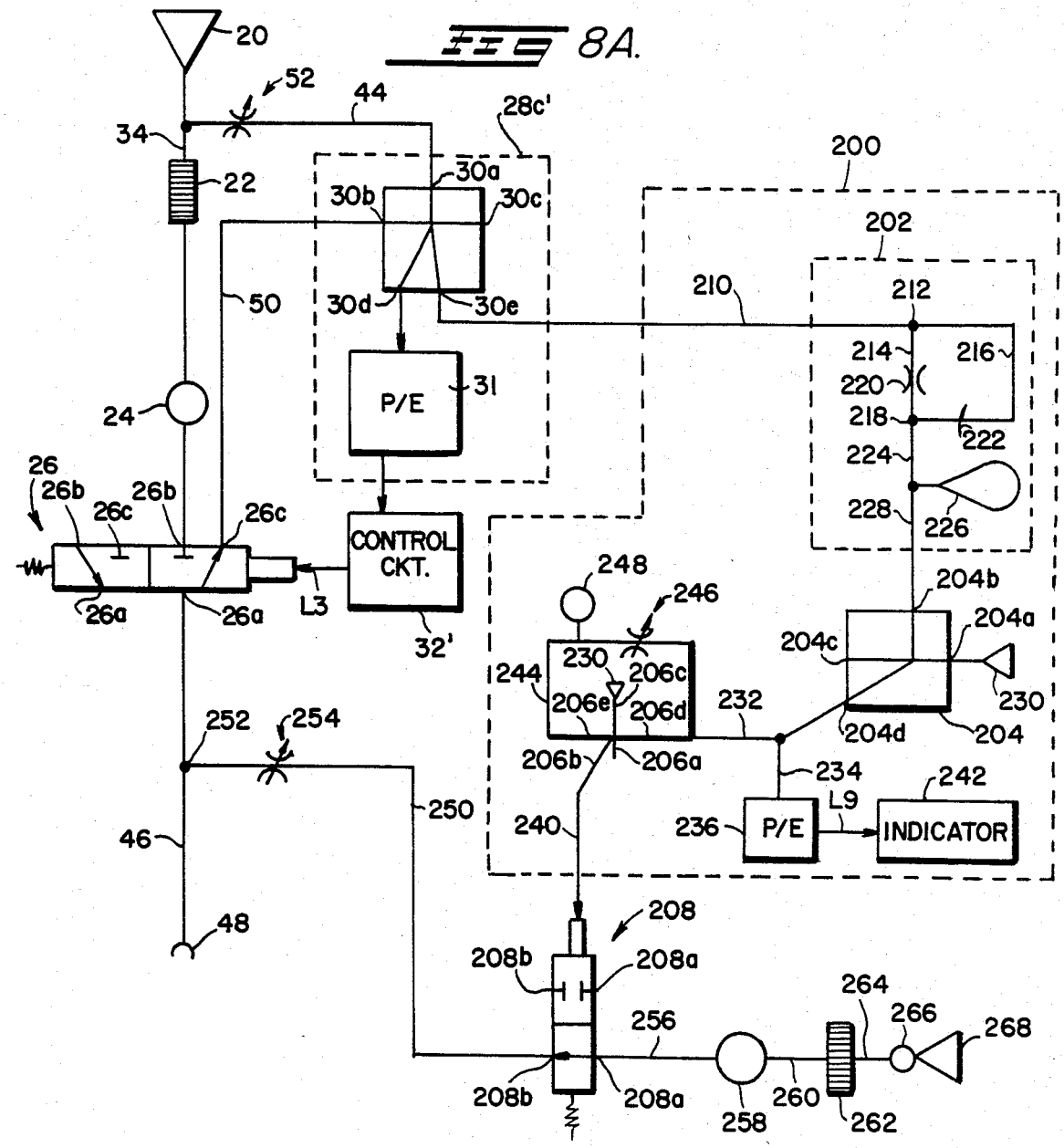

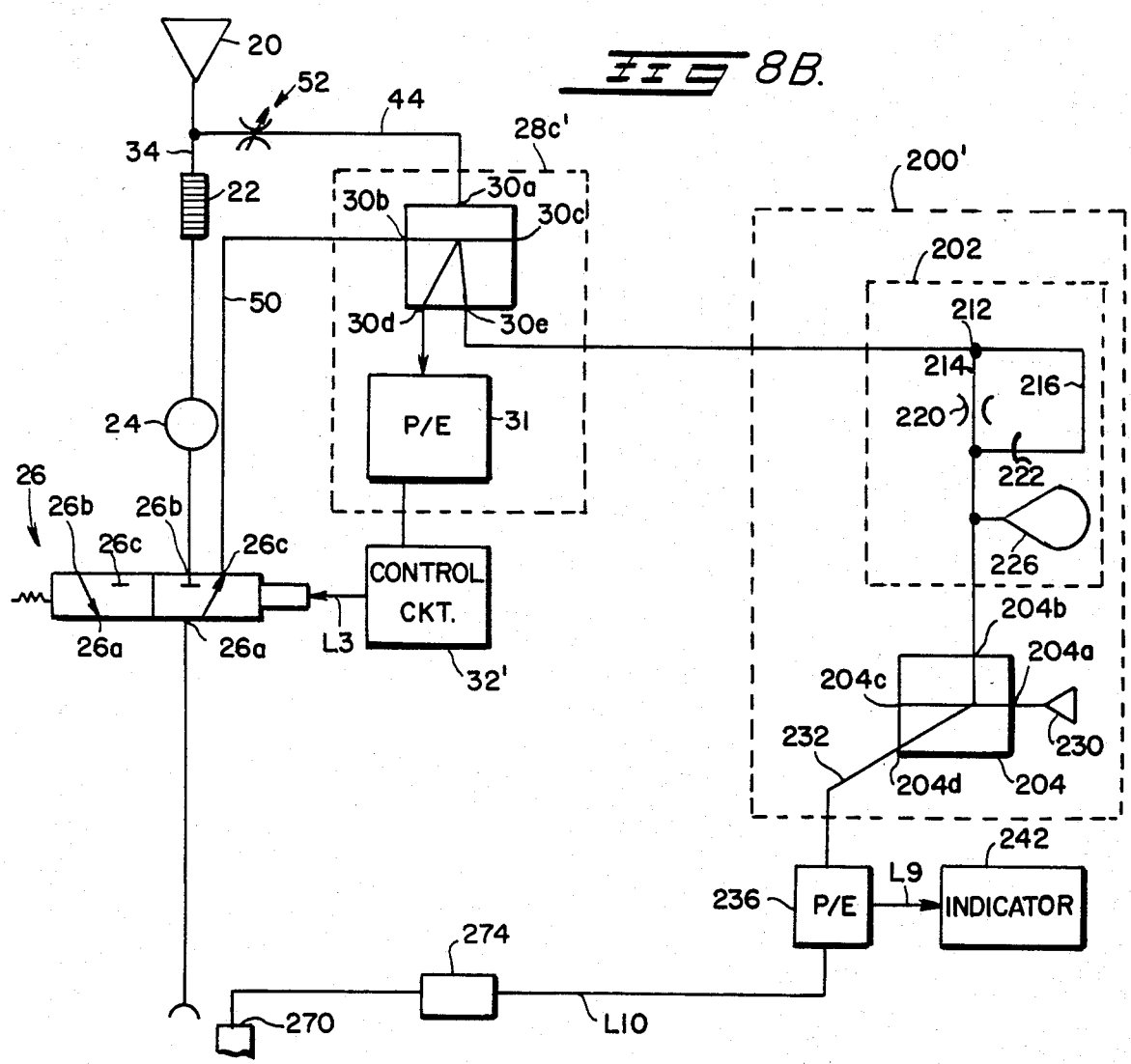

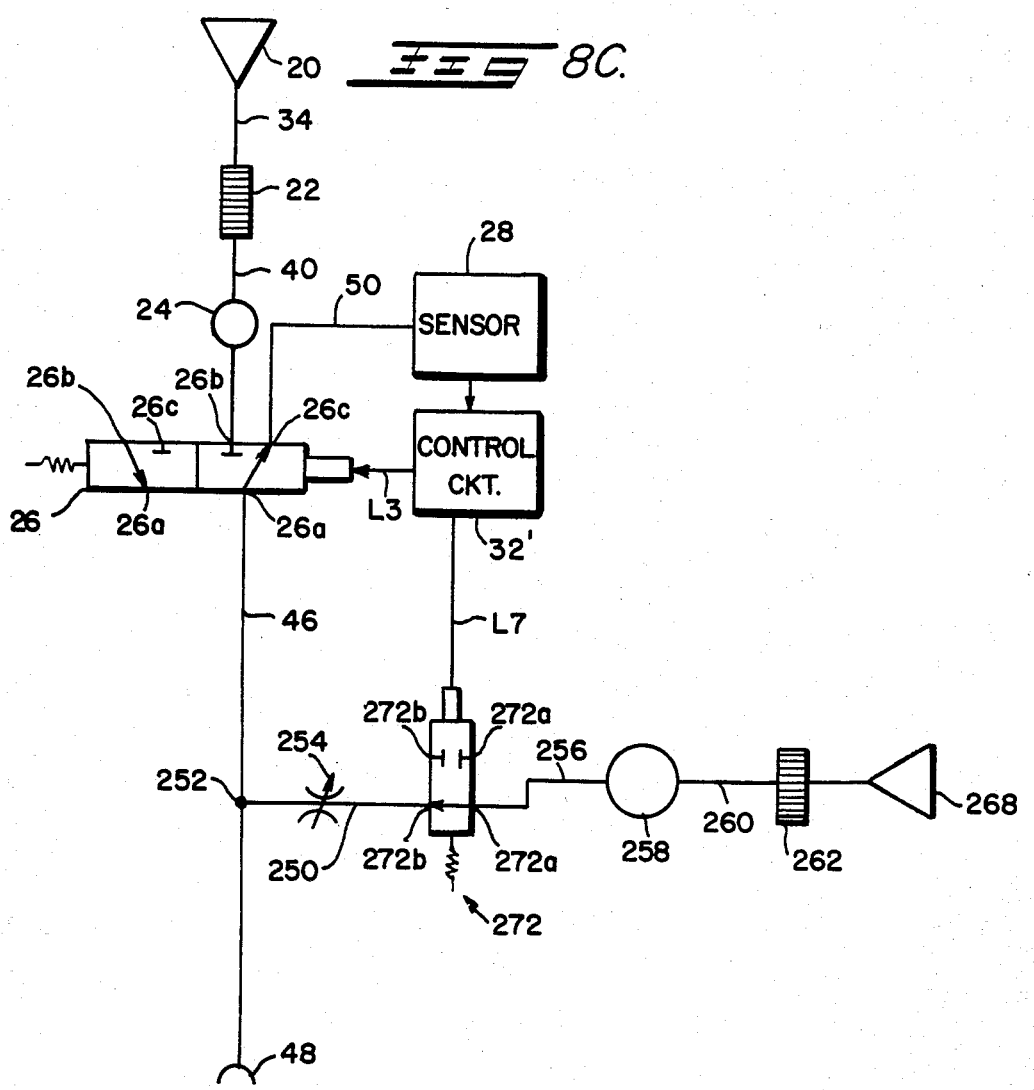

METHOD AND APPARATUS FOR RECTIFYING OBSTRUCTIVE APNEA

BACKGROUND OF THE INVENTION

This invention pertains to apnea event devices utilized to detect the cessation of breathing in an in vivo respiratory system, and to methods of operating respirating gas supply apparatus so that apnea events caused by the occlusion of upper airway passages in the in vivo respiratory system are remedied.

U.S. patent application Ser. No. 210,653, filed Nov. 26, 1980 and now U.S. Pat. No. 4,414,982 by Gerald P. Durkan and commonly assigned herewith, is incorporated herein by reference as disclosing a respirator apparatus including a predominately fluidically operated apnea event circuit which signals the occurrence of an apnea event after the lapse of a predetermined time interval since the last inspiration attempted by an in vivo respiratory system. One cause of apnea events such as those detected by the apparatus of U.S. patent application Ser. No. 210,653 is the occlusion of upper airways, such as the oropharyngeal airway, in the invivo respiratory system.

In the above respect, it has been suggested by Remmers et al. ("Pathogenesis of Upper Airway Occlusion During Sleep", *Journal of Applied Physiology* 1978; 44:931–38) that in some in vivo respiratory systems the subatmospheric or negative pressure occasioned during inspiration sucks the tongue and soft palate against the posterior oropharyngeal wall. Other causes and conditions associated with upper airway obstruction/occlusion are summarized by Sullivan et al. ("Reversal of Obstructive Sleep Apnoea By Continuous Positive Airway Pressure Applied Through the Nares", *The Lancet*, Apr. 18, 1981, pp. 862–865) which is incorporated herein by reference for a discussion of the obstruction/occlusion phenomena. Sullivan et al. report treatments for obstructive sleep apnoea syndrome wherein low levels of pressure (in the range of 4.5 to 10 cm water) were continuously applied to provide a pneumatic splint for the nasopharyngeal airway.

U.S. Pat. No. 4,155,356 to Venegas discloses a respiration assisting method and apparatus comprising means for generating a series of pressure pulses and means for transmitting the pressure pulses to air passageways in the lungs. The transmission means comprises a tube placed in the trachea so that pressure waves created by the pressure pulses outwardly displace walls of collapsed air passageways in the lungs and maintain such outward displacement during expiration. Venegas provides no means for the sensing of conditions in the lungs nor does he coordinate the application of pressure pulses in time relation with the occurrence of such conditions.

In view of the foregoing, it is an object of this invention to provide a respirating gas supply apparatus which, upon the detection of an appropriate apnea event caused by the occlusion or obstruction of upper airway passages in an in vivo respiratory system, attempts to remedy the occlusion or obstruction in the upper airway passages.

SUMMARY

Upon the detection of an appropriate apnea event, respirating gas supply apparatus according to various embodiments supply stimulus to the upper airway passages of an in vivo respiratory system in an effort to dislodge any occlusion or obstruction in the upper airway passages. In one embodiment the stimulus applied is a high pressure pulse of gas. In another embodiment an electrical signal is applied to an electromyographic electrode positioned in proximity to a nerve controlling a muscle or organ which may obstruct the upper airway passage.

In various embodiments of a respirating gas supply method and apparatus, a control circuit responsive to a sensor operates a valve to supply pulses of respirating gas through a single hose cannula to an in vivo respiratory system when negative pressure indicative of inspiration is sensed by the sensor. The control circuit operates the valve to communicate the in vivo respiratory system with a supply of gas only if the negative pressure sensed by the sensor does not occur within a predetermined yet selectively variable required minimum delay inverval between successive pulsed application of the gas to the in vivo respiratory system.

In some embodiments, a three-way valve having ports connected to the sensor, the gas supply, and the single hose cannula is used. In another embodiment, a four-way valve facilitates usage of the apparatus in conjunction with a humidifier and/or a nebulizer.

In one embodiment a respirating gas supply apparatus has a sensor comprising a biased fluidic amplifier and a pressure-to-electric (P/E) switch.

Apparatus according to the embodiments described herein can be operated to supply spiked pulses or square pulses of gas depending on whether a flowmeter is connected between the supply of gas on the valve.

The control circuit of the respirating gas supply apparatus also has means for determining if the in vivo respiratory system has failed to demand a pulse of gas after the elapse of a predetermined but selectively variable maximum time inverval. Upon detecting such an apnea event, the apparatus activates various indicator or alarm means and operates the valve to supply an additional pulse or pulses of gas to the in vivo respiratory system.

BRIEF DESCRIPTION OF THE DRAWINGS

The foregoing and other objects, features and advantages of the invention will be apparent from the following more particular description of the preferred embodiments of the invention, as illustrated in the accompanying drawings in which like reference characters refer to the same parts throughout different views. The drawings are not necessarily to scale, emphasis instead being placed upon illustrating the principles of the invention.

FIG. 1A is a schematic diagram showing a gas supply apparatus according to an embodiment of the invention wherein gas is supplied in a spiked pulse mode;

FIG. 1B is a schematic diagram showing a gas supply apparatus according to an embodiment of the invention wherein gas is supplied in a square pulse mode;

FIG. 1C is a schematic diagram showing a gas supply apparatus according to an embodiment of the invention wherein sensing means comprises a fluidic amplifier;

FIG. 2 is a schematic diagram showing a gas supply apparatus according to an embodiment of the invention wherein supply gas is humidified;

FIG. 3 is a schematic diagram showing a gas supply apparatus according to another embodiment of the invention wherein supply gas is humidified;

FIG. 5 is a schematic diagram showing a control means according to an embodiment of the invention;

FIG. 6 is a schematic diagram showing a gas supply apparatus according to another embodiment of the invention wherein a second gas is also supplied;

FIG. 7A is a plan view of a fluid amplifier of the embodiment of the gas supply apparatus of FIG. 1C;

FIG. 7B is a graph illustrating the output pressure gain curve for the fluidic amplifier shown in FIG. 7A; and, FIGS. 8A, 8B, and 8C are schematic diagrams showing differing embodiments of gas supply apparatus which detect apnea events and attempt to remedy apnea events caused by occlusion of upper airway passages in the in vivo respiratory system.

DETAILED DESCRIPTION OF THE DRAWINGS

Figure 4A:
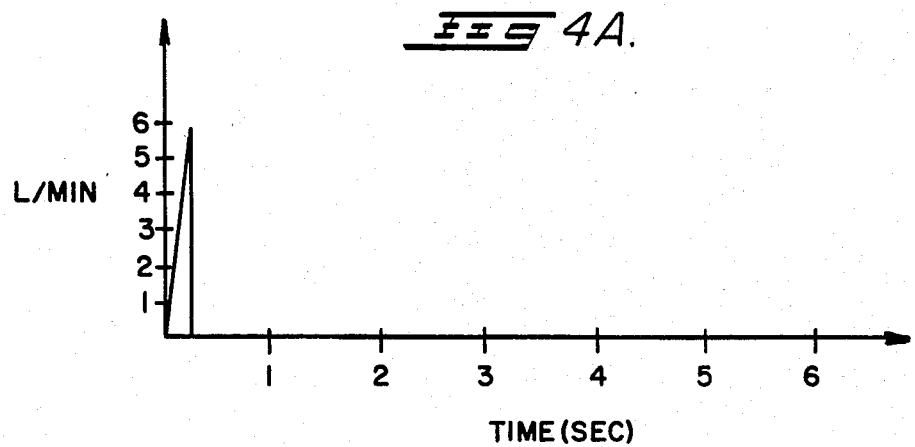
FIG. 4A is a graph illustrating a spiked pulse method of supplying gas according to a mode of the invention.

The respirating gas supply system of the embodiment of FIG. 1A comprises a source of gas 20; a flowmeter 22; a fluidic capacitance 24; valve means 26; sensing means 28; and, control means 32.

Source 20 is typically a source of oxygen gas. Depending upon the particular environment of use, source 20 may be a portable tank or a wall supply, for example. Source 20 is connected by line 34 to the flowmeter 22. As used herein unless otherwise indicated, any fluid conveying means, such as a duct, pipe, channel, or other closed fluid conduit, is referred to as a line.

While the flowmeter 22 may be of any conventional type, a ball float-type flowmeter manufactured by Dwyer is suggested as one acceptable model. The flowmeter illustrated in FIG. 1A comprises a needle valve (not shown) which has an inherent resistance FR to the flow of gas. The flowmeter inherent resistance is dependent, inter alia, on the dimensions of the needle valve and the needle orifice. The flowmeter 22 is connected to the capacitance by line 40.

Capacitance 24 is shown as a tank but in another embodiment is merely a relatively long length of tubing. As seen hereinafter, the volume of capacitance 24, the flowmeter inherent resistance FR, the inherent resistance VR of the valve 26, and the interrelationship between these factors influence the amplitude of a pulse of gas produced by the respirating gas supply system of FIG. 1A.

The valve means 26 of the embodiment of FIG. 1A is a three-way two position solenoid-actuated spool valve having ports 26a, 26b, and 26c in its bore. Port 26a is connected by line 46 (a single hose) to a means 48 for applying gas to an in vivo respiratory system. Although the particular means shown in FIG. 1A is a single hose cannula, it should be understood that other suitable devices, such as an endotracheal tube or a hand resuscitator, for example, may be employed. The aforesaid line 40 ultimately connects port 26b to the source 20. Port 26c is connected by line 50 to the sensing means 28.

As shown in the FIG. 1 representation of the valve 26, the spool of valve 26 is biased to its first position to connect port 26a to port 26c so that the cannula 48 (and hence in vivo respiratory system (not shown) including nares in which the cannula 48 is inserted) is in fluidic communication with the sensing means 28. It should be understood that the valve 26 can be operated to move the spool to its second position to connect port 26a with port 26b so that a pulse of gas is supplied to the in vivo respiratory system through the single hose 46. When connected in this manner, the valve 26 has an inherent resistance VR to the flow of gas which is dependent on the size of the orifice connecting port 26a to port 26b.

The valve 26 is electrically controlled by control means 32 in the manner hereinafter described. While the valve 26 shown in FIG. 1A is of a type manufactured by Lee as model LFAA 1200318H, any comparable model can be used.

The sensing means 28 of FIG. 1 comprises suitable means for sensing a negative fluidic pressure applied along line 50 and for generating an electrical signal in accordance with the sensing of the negative fluidic pressure. In one embodiment the sensor 28 comprises a pressure-to-electric (P/E) switch, such as a Model E P/E Switch manufactured by the Dietz Company which can sense pressures as low as 0.02 inches (column of water). In this embodiment, the negative input port of the P/E switch is connected to the line 50 while the positive input port is left open to ambient. Large diaphragms used in state-of-the-art P/E switch technology, such as the two inch diameter diaphragm of the Dietz Model E P/E, have considerable internal volume and hence, for some environments of use, a significantly long time response. Many P/E switches must also be mounted horizontally to achieve maximum sensitivity, but mounting the switches horizontally presents another problem—acceleration sensitivity of the diaphragm.

The sensing means 28C of FIG. 1C comprises means 29 for sensing positive fluidic pressure and for generating an electrical signal in accordance with the sensed fluidic pressure, as well as amplification means such as fluid amplifier 30. The fluid amplifier 30 depicted in FIG. 1C is a biased turbulent proportional amplifier shown in more detail in FIG. 7A.

The biased fluidic amplifier 30 has a power input stream 30; two control ports 30b and 30c; and, two output ports 30d and 30e. The power stream input port 30a is connected by the line 44 ultimately to the source 20. A variable restrictor 52 on line 44 is used to limit the magnitude of flow and pressure of flow of the input stream and thus the sensitivity of the fluidic amplifier 30. Control port 28b is connected by line 50 to port 26c of the valve 26 such that negative pressure in line 50 (created by inspiration in the in vivo respiratory system) deflects the power stream to output port 30d. The amplifier 30 is biased such that non-negative pressure in line 50 results in the power stream passing through the output port 30e.

The amplifier structure of FIG. 7A illustrates the biased nature of the amplifier 30. The amplifier 30 is configured with an off-set splitter. That is, the power input stream 30a is canted so that, absent control signals at ports 30b (also labeled $C_r$) and 30c ($C_l$), the output is normally biased to the left output port 30e (L). When negative pressure is applied through port 30b, the output switches to port 30d. When the negative pressure ceases, the output automatically switches back to port 30e. In a preferred embodiment the amplifier 30 operates with a low power supply so that the jet is laminar. The output pressure gain curve for the fluid amplifier 30 of FIG. 7A is shown in FIG. 7B.

A fluidic amplifier of the type manufactured by Tri-Tec, Inc. as Model No. AW12* functions well as the amplifier 30 of FIG. 7A to give a sensitivity to negative pressures at least as low as 0.02 cm water. It should be understood by those skilled in the art that other fluidic elements, such as a NOR gate, can be configured with the circuitry shown to yield acceptable results.

In the embodiment of FIG. 1C a pressure-to-electric (P/E) switch 31 is used as the means for sensing positive pressure and for generating an electrical signal in accordance with the sensed fluidic pressure. The P/E switch 31 illustrated in FIG. C is a conventional P/E switch such as that manufactured by Fairchild as Model PSF 100A. The positive input port of the P/E switch 31 is connected to the output port 30d of sensor 30 by line 54 while the negative input port thereof is open to ambient. For the particular sensing means 28 illustrated in FIG 1C, the P/E switch 31 shuld be sensitive enough to switch when positive pressure as low as 0.02 cm. of water is incident thereon. When P/E switch 31 receives such pressure, P/E switch 31 closes a switch 36 as seen hereinafter with reference to FIG. 5.

Referring now again to the embodiment of FIG. 1A, it should be understood that other types of sensing means 28 may be employed. Those skilled in the art recognize that (if operating requirements permit) a thermistor system can be utilized, provided the thermistor system is made direction sensitive (by utilizing two thermistors and appropriate time delay measurement circuitry). Ordinarily, however, the flow-type (as opposed to pressure-type) sensitivity of a thermistor prevents the thermistor from sensing flow rapidly enough to facilitate the supply of an oxygen pulse early in inspiration, such as in the manner taught in U.S. patent application Ser. No. 210,654. In another embodiment, a pressure transducer functions as the sensing means 28. The pressure transducer can be a solid state, a capacitance, or an electromechanical (diaphragm-type) transducer, depending on the sensitivity required. Transducers provide an analog signal and require rather complex electrical circuitry. A suitable solid state crystal may someday be developed to function as the sensing means 28 in accordance with desired sensitivity requirements.

The respirating gas supply system of FIG. 1B resembles the system of FIG. 1A but does not have the flowmeter 22. As seen hereinafter, the system of FIG. 1A produces a spiked pulse of gas whereas the system of FIG. 1B produces a square pulse of gas.

The respirating gas supply system of the embodiment of FIG. 2 basically resembles the system of FIG. 1B but, rather than employ a three-way valve, utilizes a four-way two-position valve 58 as its valve means. The four-way valve 58 has four ports in its bore: port 58a connected by the line 46 to the cannula 48; port 58b connected by line 42 ultimately to the source 20; port 58c connected by line 50 to control port 28b of sensor 28; and, port 58d connected by a line 60 to an input of a humidifier 62. Valve 58 can be any conventional four-way two position valve, such as the solenoid-actuated spool valve model 8345E1 manufactured by ASCO. As shown in the FIG. 2 representation of valve 58, the valve 58 is biased in a first position to connect port 58a to port 58c so that cannula 48 (and hence the in vivo respiratory system) is in fluidic communication with the sensor 28. It should be understood that the valve 58 can be actuated to a second position to connect port 58b to port 58d. When this occurs, gas is supplied through the valve 58 and line 60 to the input of humidifier 62.

Humidifier 62 is a bubble type humidifier, such as the model 003-01 humidifier available from Respiratory Care, Inc. Humidifier 62 yields a humidified gas flow on line 64 connected to the output of the humidifier 62. Line 64 connects with a line 46 at point 66. A variable resistance 64R on line 64 insures that upon inspiration the path of least resistance through line 46 and the valve 58 rather than through line 46.

It should be understood that the apparatus of the embodiment of FIG. 2 can be connected in the manner of FIG. 1A (that is, with a flowmeter) to operate in a spiked pulse mode rather than a square pulse mode.

The respirating gas supply system of the embodiment of FIG. 3 basically resembles the system of FIG. 1B but further incorporates the humidifier 62. A line 65 connects to line 46 at point 67. The line 65 connects the point 67 to the input of the humidifier 62. Line 64 from the output of the humidifier 62 terminates in a nozzle 68 of a venturi 70. The venturi 70 is connected on line 46 intermediate the port 58a of valve 58 and the cannula 48. A variable resistance 65R on line 65 insures that upon inspiration the path of least resistance is through the line 46 and the valve 26 rather than through line 65. Resistance 65R also serves to control the flow into the humidifier 62 through line 65. The venturi 70 shown is a type F-4417-10 available from Airlogic, although any comparable venturi is suitable. Again, it should be understood that the embodiment of FIG. 3 can, if desired, incorporate a flowmeter in order to operate in a spiked pulse mode.

It should be understood by those skilled in the art that a device for administering medication, such as a nebulizer, can be connected in the systems of FIGS. 2 or 3 in essentially the same respective manners as the humidifier 62 shown therein.

The respirating gas supply apparatus of the embodiment of FIG. 6 basically resembles the embodiment of FIG. 1B but further includes means for suppling a second gas to the in vivo respiratory system. The apparatus of FIG. 6 further comprises a source 120 of a second gas (such as an anesthetic gas, for example), a capacitance 124; and, second valve means 126. Source 120 is connected to capacitance 124 by line 134; capacitance 124 is connected to the valve means 126 by line 142. The apparatus of the embodiment of FIG. 6 can be used, if desired, with a humidifier in the manner described above with reference to either FIG. 2 or FIG. 3.

Valve 126 is a two-way two position solenoid-actuated spool valve having port 126a and 126b in its bore. The central spool of valve 126 is biased in a first position as shown in FIG. 6 so that ports 126a and 126b are not communicating. Port 126b of valve 126 is connected by line 144 to a point 146 where line 144 joins line 46. A variable resistance 147 on line 144 insures that upon inspiration the path of least resistance is through the line 46 and valve 26 rather than through line 144. The solenoid valve 126 is electrically connected by lines L3' and L3 to the control means 32. In other embodiments the solenoid valve is mechanically connected to a control means.

The control means 32 of the embodiment of FIG. 5 is suitable for use with apparatus constructed in accordance with any of the foregoing embodiments. Control means 32 is a circuit comprising four NAND gates (72, 74, 76, and 78); four NOR gates (80, 82, 84, and 86); three transistors (T1, T2, and T3); a 555 timer chip 88; a 556 dual timer chip 90; LEDs 92 and 94; piezo electric member 96; and, various resistances and capacitances as hereinafter designated.

As used with reference to FIG. 5, the notation "LX" denotes an electrical line (as opposed to a fluidic line) where X is a appropriate reference number. For example, controller 32 includes a line L1 connected to a high DC voltage supply (not shown) and line L2 connected to a low DC voltage supply (also not shown). The potential difference across L1 and L2 is between 12 and 15 volts DC.

The 556 dual timer chip 90 shown in FIG. 5 is a 14 pin chip manufactured by National Semiconductor as part number LM 556CN. It should be understood that any comparable 556 dual timer chip is suitable for the circuit of FIG. 5. For the particular chip shown, pins 1-7 correspond to pins of a first timer in the dual timer while pins 8-14 correspond to pins of a second timer. The pins are labeled as follows:

| PIN DESCRIPTIONS FOR 556 CHIP | | |
|---|---|---|
| DESCRIPTION | TIMER 1 | TIMER 2 |
| discharge | 1 | 13 |
| threshold | 2 | 12 |
| control voltage | 3 | 11 |
| reset | 4 | 10 |
| output | 5 | 9 |
| trigger | 6 | 8 |
| ground | 7 | |
| operating voltage | | 14 |

The pin connections for the first timer of the 556 dual timer 90 are as follows: Pins 1 and 2 are connected to line L2 through a series combination of resistor R1 and a 100K variable potential resistance R2. Pins 1 and 2 are also connected to line L2 through capacitance C1. Pin 3 is connected to line L2 through capacitor C2. Pin 4 is connected directly to line L1. Pin 5 is connected to the base of transistor T1 through resistor R3. Pin 3 is also connected to the anode of LED 92 (the cathode of LED 92 being connected through resistor R4 to the line L2). Pin 6 is connected through capacitor C3 to the output terminal of NOR 80. Pin 6 is also connected to line L1 through the resistor R14 and to line L2 through the resistor R15. Pin 7 is connected directly to line L2.

The pin connections for the second timer of the 556 dual timer 90 are as follows: Pin 8 is connected through capacitor C4 to the output terminal of NOR 84, as well as to line L1 through the resistor R16 and to line L2 through the resistor R17. Pin 9 is connected to both input terminals of NAND 74. Pin 10 is connected directly to line L1 and to a point 102 discussed hereinafter. Pin 11 is connected through capacitance C5 to line L2. Pins 12 and 13 are connected to line L1 through a series combination of resistor R5 and a 100K variable potential resistor R6. Pins 12 and 13 are also connected to line L2 through capacitance C6. Pin 14 is connected directly to line L1.

The 555 timer chip 88 shown in FIG. 5 is an eight pin chip manufactured by National Semiconductor as part number LM 555CN. It should be understood that any comparable 555 chip is suitable for the circuitry of FIG. 5. For the particular chip shown the pins are labeled as follows:

| DESCRIPTION | PIN |
|---|---|
| ground | 1 |
| trigger | 2 |
| output | 3 |
| reset | 4 |
| control | 5 |
| threshold | 6 |
| discharge | 7 |
| operating voltage | 8 |

The pin connections for the 555 timer chip 88 are as follows: Pin 1 is connected directly to line L2. Pin 2 is connected to the output of NOR 82 and to the base of transistor T2. Pin 3 is connected to both inputs of NOR 86 and to a point 98. Pin 4 is directly connected to line L1. Pin 5 is connected to line L2 through capacitor C7. Pins 6 and 7 are connected to line L2 through capacitance C8. Pins 6 and 7 are also connected to line L1 through a series combination of resistances, the combination including a resistor R7 and anyone of a group of parallel-arranged resistances such as resistances Ra, Rb, and Rc . . . which of the parallel-arranged resistances is used depends on the manual positioning of a switch 100 as described hereinafter. Pins 6 and 7 are also connected to the emitter of transistor T2. Pin 8 is connected directly to the line L1.

NAND 72 has a first input terminal 72a connected to line L1 through resistance R8 and connected to L2 through the switch 36. A second input terminal 72b of the NAND 72 is connected to the output terminal of NAND 74. The output terminal of NAND 72 is connected to a first input terminal 80a of NOR 80, as well as to both input terminals of the following: NOR 82, NOR 84, and NAND 76. The first input terminal 80a of NOR 80 is also connected to a point 104 intermediate the output terminal of NOR 86 and the anode of LED 94. The second input terminal 80b of NOR 80 is connected to line L2 through resistor R9. The lines L4, L5, L6, and L7 shown in FIG. 5 are connected to further devices, such as instrumentation which, unless otherwise noted herein, do not form part of the present invention.

Transistor T1 is a NPN transistor, such as the type available from GE as part GE-66A. The emitter of transistor T1 is connected directly to line L2. The collector of transistor T1 is isolated from line L2 by a diode D1 (IN 4005) and is connected to the positive terminal of appropriate valve means (such as valve 26 or valve 58) by line L3. Line L8 is connected to the negative (or ground) terminal of the appropriate valve means.

Transistor T2 is a PNP transistor, such as the type available from GE as part GE-65. The emitter of transistor T2 is connected to pins 6 and 7 of timer 88. The base of transistor T2 is connected to the output of the NOR 82. The collector of the transistor T2 is directly connected to line L2.

FIG. 5 also includes an alarm circuit generally denoted as 100. A point 102 of alarm circuits 100 is connected both to line L1 and (through capacitor C9) to line L2. Terminal 96b of the piezo electric 96 is connected to point 102 through resistance R10 and to the base of transistor T3 through resistor R11. Terminal 96a of the piezo 96 is connected to point 102 through resistance R12. Terminal 96c of the piezo electric 96 is connected to point 98 and to the emitter of transistor T3. The alarm circuit 100, when activated, functions as an oscillator and drives therefor to produce audible oscillation. It should be understood thay any conventional circuit, including buzzers and electromechanical alarms, may be utilized instead.

Transistor T3 is a NPN transistor, such as the type available from GE as part GE-66A. The collector of transistor T3 is connected through resistor R12 to the point 102. The other connections of the transistor T3 are described above.

The NOR gate 86 has its output terminal connected to the anode of the LED 94. The cathode of the LED 94 is connected through resistor 13 to the line L2.

Conventional NOR gates can be used for the NORs 80, 82, 84 and 86 and conventional NAND gates can be used for the NANDs 72, 74, 76 and 78 utilized in the controller of FIG. 5. For the embodiment of FIG. 5, however, the NANDs illustrated are parts 4011 manufactured by National Semiconductor and the NORs are parts 4001B manufactured by National Semiconductor.

The suggested values for the resistances and capacitances for the embodiment of FIG. 5 are as follows:

| RESISTANCES | CAPACITANCES |
|---|---|
| R1 = 10K | C1 = 10μ |
| R2 = (variable) | C2 = 0.02μ |
| R3 = 1K | C3 = 0.1μ |
| R4 = 2K | C4 = 0.1μ |
| R5 = 10K | C5 = 0.02μ |
| R6 = (variable) | C6 = 22μ |
| R7 = 1.2K | C7 = 0.02μ |
| R8 = 2K | C8 = 220μ |
| R9 = 20K | C9 = 10μ |
| R10 = 220K | |
| R11 = 10K | |
| R12 = 510K | |
| R13 = 2K | |
| R14 = 1 M | |
| R15 = 1 M | |
| R16 = 1 M | |
| R17 = 1 M | |

In the operation of the respirating gas supply system of the embodiment of FIG. 1A, gas from the source 20 is passed through line 34 to the flowmeter 22. The needle valve (not shown) in flowmeter 22 is set to control the rate of flow through the flowmeter 22. Gas flowing through the flowmeter 22 continues through line 36 to the capacitance 24. From capacitance 24 the gas passes into line 42. The gas in line 42 does not pass through the valve 26 until the valve 26 is actuated so that port 26b thereof is connected to port 26a in the manner hereinafter described.

The cannula 48 is inserted in the nares of an in vivo respiratory system. When a negative pressure is created by an attempted inspiration by the in vivo respiratory system, the negative pressure is applied to the single hose 46.

For the apparatus shown in the embodiment of FIG. 1A, valve 26 is normally in the position shown in FIG. 1A with port 26a connected to port 26c. Upon inspiration a negative pressure is created in line 50. In the embodiment described above wherein sensor 28 is a P/E switch, for example, the negative pressure in line 50 acts upon the negative pressure input port of the P/E switch. The P/E switch accordingly closes the switch 36 of FIG. 5.

For the apparatus shown in the embodiment of FIG. 1C, the negative pressure in line 50 created by inspiration is applied to the control port 30b of fluidic amplifier 30. The negative pressure at control port 30b causes the power stream input of amplifier 30 to be deflected so that output occurs at the output port 30d rather than at the output port 30e to which it is normally biased. The output from port 30d creates a positive fluid signal on line 54 which is applied to the positive input port P/E switch 31. The P/E switch 31 accordingly closes the switch 36 of FIG. 5.

With respect to the controller 32 as depicted in FIG. 5, the closing of switch 36 completes a circuit between lines L1 and L2 and causes a false signal to be applied to input port 72a of NAND 72. Since the input port 72b normally receives a true signal (except when the negative pressure is sensed during a required minimum delay interval after the next preceeding application of gas in the manner hereinafter described), the output of NAND 72 is true. Accordingly, input terminal 80a of NOR gate 80 goes true. Likewise, all input terminals of NAND 76, NOR 82, and NOR 84 are true.

Unless an apena event is detected as hereinafter described, or unless a true signal is received on line L4, the input terminal 80b is false. At this point, the output of NOR gate 80 is false. The output of NOR 84 is also false.

False outputs from the NOR gates 80 and 84 are applied to pins 6 and 8 of the dual timer 90. Pin 6 is the trigger input of the first timer included in the dual timer 90; pin 8 is the trigger input of the second timer included in the dual timer 90. As result of trigger pins 6 and 8 going from true to false, the outputs from corresponding pins 5 and 9 go true.

Output pin 5 of the dual timer 90 going true causes transistor T1 to conduct, so that a current is established on line L3. The resultant electrical signal on line L3 causes the solenoid valve 26 to move from its normally biased position as shown in FIG. 1A to its second position where port 26b thereof is connected to port 26a.

Connecting port 26b of the solenoid valve 26 to port 26a enables the gas in line 42 to be transmitted through the valve 26. It should be recalled that both the flowmeter 22 and the valve 26 have inherent resistances to the flow of gas. The resistance FR of the flowmeter is generally greater than the resistance VR of the valve 26. Thus, as the valve 26 moves to connect port 26a to ports 26b, pressure in line 42 drops and, if the valve 26 remains in this position long enough, the rate of flow of the gas eventually is dictated by the resistance FR of the flowmeter 22.

Valve 26 thus allows a pulse of gas to pass from line 42 through valve 26, through line 46 and cannula 48, and into the in vivo respiratory system. As seen hereinafter, the duration of the pulse is determined by the length of the time the valve 26 remains in the position wherein port 26b is connected to port 26a. The amplitude of the pulse is a function of the flow rate through the valve 26. Incorporation of the flowmeter 22 and to the fluid supply circuit of FIG. 1A causes the pulse of gas produced to have a spike shape such as that shown in FIG. 4A. While the pulse of gases is being supplied, the LED 92 conducts to provide a visual indication of the same since the signal applied to transistor T1 is also applied to the LED 92 anode.

When the output pin 5 of the dual timer 90 goes false the pulse of gas supplied through the valve 26 is caused to terminate. In this respect, a false signal from pin 5 stops the transistor T1 from conducting, so that the signal on line L3 goes false. A false signal on line L3 causes the solenoid valve 26 to return to its normally biased position as shown in FIG. 1A.

The time at which the output pin 5 of dual timer 90 goes false depends on the voltage value supplied to pin 2 of the dual timer 90. The voltage value at pin 2 of the dual timer 90 is dependent on the value chosen for the 100K variable potential resistor R2. In this respect, the pulse of gas is supplied until the voltage at pin 2 becomes two-thirds of the voltage difference seen across pins 7 and 14. For the embodiment described herein with reference to the circuit values mentioned above, when the resistance value of resistor R2 is 35K, for example, a pulse of 0.5 seconds duration will be supplied.

As mentioned above, both timers in the dual timer 90 were triggered so that the output pins 5 and 9 became true. A true signal on pin 5 moved the solenoid valve 26 as described hereinbefore. A true on pin 9, however, causes the NAND gate 74 to go false, so that a false signal is supplied to the input terminal 72b of NAND 72. The output of NAND 72 thus goes true and remains true as long as pin 9 of the dual timer 90 is true.

While the output of NAND 72 remains true, pin 6 of the dual timer 90 cannot be triggered false. In this respect, pin 6 of the dual timer 90 remains false and cannot transition from true to false while pin 9 is true. This means that should the in vivo respiratory system attempt to inspire while pin 9 of dual timer 90 is still true, the attempted inspiration will have no effect on pin 6 of the dual timer 90, and hence no effect on the valve 26 so that an additional pulse of gas is not supplied. Further attempted inspirations are ineffectual until the output pin 9 of dual timer 90 goes false. The time at which the output pin 9 of dual timer goes false is selectively variable by the value chosen for the 100K potential variable resistor R6. R6 affects the voltage value applied to the threshold pin 12 of the dual timer 90, which determines when the output pin 9 goes false.

The value chosen for the resistor R6 determines a required minimum interval between successive applications of gas to the in vivo respiratory system. This enables the apparatus to supply a fixed volume dose of respirating gas to the in vivo respiratory system per unit time. For the suggested circuit values given hereinbefore, resistor R6 chosen to have a value of 73K gives a delay interval of 2.0 seconds. That is, when a negative pressure is sensed in the in vivo respiratory system, controller 32 will not permit a pulse of gas to be applied to the in vivo respiratory system unless the required delay interval has elapsed since the sensing of negative pressure which resulted in the next preceding application of gas to the in vivo respiratory system. In this manner, the in vivo respiratory system is protected from over oxygenation should the in vivo respiratory system attempt an abnormally true number of inspirations. Without this protection feature, the in vivo respiratory system would dangerously be supplied excess pulses of gas when attempted inspirations are too frequent.

The foregoing method of requiring the elapse of a minimum delay interval between successive applications of gas to the in vivo respiratory system also enables the apparatus of the embodiment discussed herein to be operated when desired in accordance with the method described in U.S. patent application Ser. No. 210,654, already incorporated herein by reference. The pulse has a duration which can be less than the duration of the inspiration.

When the apparatus of the embodiment of FIG. 1A, for example, is operated in accordance with a mode of the method of patent application Ser. No. 210,654, the valve 26 returns to its normally biased position with port 26a connected to port 26c long before the negative pressure in the in vivo respiratory system has ceased. In this respect, the pulse of gas is supplied for a time period which is a fraction of the duration of inspiration. Without the protective function of the second timer (and the effect of output pin 9 of the dual timer 90 on NAND 80 to prevent trigger pin 6 of the dual timer 90 from going from true to false), an additional pulse of gas would be supplied for the same inspiration. Thus, the protective function provided by the second timer of the dual timer 90 of controller 32 allows the valve 26 to return to its normally biased position and provides a buffer time interval in which the valve 26 cannot again be actuated. Thus, controller 32 facilitates the usage of a single simple valve rather than a series of valves. Moreover, controller 32 and the valve means associated therewith facilitates the use of a single hose 46 leading to a single hose cannula 48, which allows both negative pressure and positive pressure to be transmited through the same line 46.

Figure 4B:
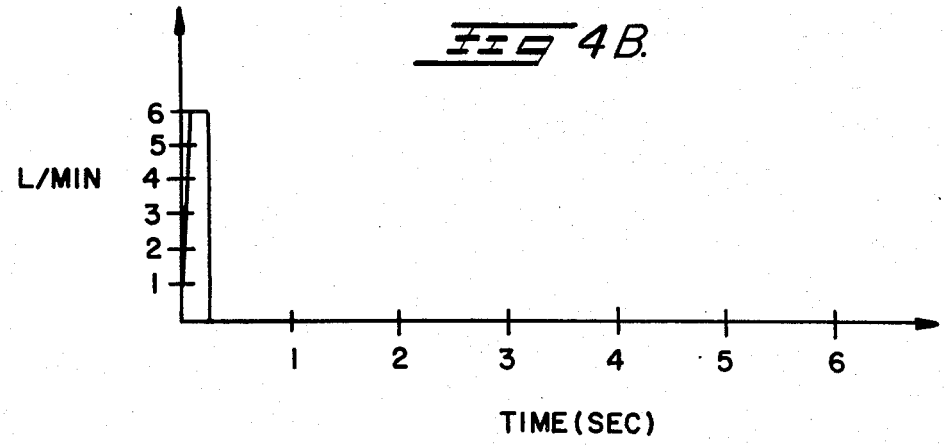
FIG. 4B is a graph illustrating a square pulse method of supplying gas according to a mode of the invention.

The operation of the embodiment of FIG. 1B basically resembles that of the embodiment of FIG. 1A, but, rather than supplying a spiked pulse, the embodiment of FIG. 1B supplies a square pulse such as that shown in FIG. 4B. The square pulse results from the fact that there is no flowmeter in the line connecting the source 20 the the valve 26. Thus, the pressure in the capacitance 24—whether it be merely a length of tubing or a tubing and a tank—is the pressure of the source 22 rather than the pressure determined by the inherent resistance of the flowmeter. Thus, when valve 26 is opened to connect port 26a and port 26b, the only limiting influence on the flow of gas is the inherent resistance of the valve 26. Without the inherent resistance FR of the flowmeter to dampen the pulse, the pulses assumes a square shape. It is currently thought that the square shape mode allows a more accurate dosage of volume flow to the cannula 48.

The operation of the embodiment of FIG. 2 also basic resembles that of FIG. 1A but further supplies a humidified pulse of gas to the in vivo respiratory system. In the same manner described with reference to the FIG. 1A embodiment, controller 32 causes valve 58 to move to a position where a port 58b communicates with port 58d when an appropriate negative pressure is detected in the in vivo respiratory system. A pulse of gas then passes through line 60 to humidifier 62. A humidified pulse of gas leaves humidifier 62 and travels to the in vivo respiratory system on line 64 and 46. In this manner moisture provided by the humidifiers 62 does not contaminate ports 58a and 58c of valve 58, nor the sensor 28 connected thereto by line 50.

It should be apparent by the operation of the embodiment of FIG. 1A that the operation of the embodiment of FIG. 3 is substantially the same except that in the FIG. 3 embodiment the pulse of gas is also humidified by humidifier 62 before it passes to the in vivo respiratory system. The pulse of gas leaves the valve 26 through line 46. A point 67 the pulse divides so that a pulse first portion continues to travel on line 46 to the input of venturi 70 and a pulse second portion is supplied on line 65 to the input of the humidifier 62. The resulting humidified gas from the humidifier 62 is applied on line 64 to nozzle 68 of the venturi 70. The pulse of gas leaving venturi 70 is thus humidified for application to cannula 48. Use of venturi 70 in this manner eliminates the need of additional or more complicated valving means and protects the humidifier 62 from higher pressures it might otherwise receive.

With respect to the embodiment of FIG. 6, a true signal on line L3 causes not only the valve 26 to allow the passage of a pulse of a first gas therethrough, but also causes the valve 126 to be actuated to connect the source 120 of the second gas to the cannula 48. In this respect, the true signal on lines L3 and L3' cause valve 126 to be actuated so that port 126a is communicable with port 126b. A pulse of second gas is thereby supplied through lines 144 and 46 to the cannula 48.

The duration of the pulse of the second gas is determined in the same manner as the duration of the pulse of the first gas. The amplitude of the pulse of the second gas is determined in much the same manner as the amplitude of the first gas, being dependent on the inherent resistance VR of the valve 126 and the pressure of the source 120. It should be understood that, if desired, the apparatus of FIG. 6 can operate in the spiked pulse mode by connecting a flowmeter between valve 126 and source 120.

The system of FIG. 6 provides the same protective features for the in vivo respiratory system as do any of the foregoing embodiments. Additionally, the second gas (such as an anesthetic), is supplied only when the first gas (such as oxygen) is also being supplied.

It has been described above how the controller 32 protects the in vivo respiratory system from overoxygenation should the in vivo respiratory system attempt an abnormally high number of inspirations. The following discussion illustrates how the controller 32 indicates that the in vivo respiratory system is failing to attempt a further inspiration within a maximum time interval.

As mentioned above, when an inspiration (negative pressure from the in vivo respiratory system) is sensed, both input terminals of NOR 82 are true. The resultant false output of NOR 82 is applied to input pin 2 of the timer 88, as well as to the base of transistor T2. Transistor T2, being a PNP type, conducts to discharge capacitor C8. The transition from a true to a false input ot pin 2 of timer 88 results in a true output on pin 3 of timer 88. The true output signal from pin 3 is applied to alarm circuit 100 so that the piezo element 96 therein remains inactive. Likewise, the true output signal from pin 3 is applied to both input terminals of NOR 86, resulting in a false output signal from NOR 86 at point 104. The false output from NOR 86 does not trigger the LED 94 nor does it affect input terminal 80b of NOR 80.

When negative pressure is not sensed in the in vivo respiratory system, the output signal from NAND 72 is false. This false output signal, applied to both input terminals of NOR 82, results in a true output from NOR 82. The true output signal from NOR 82 is applied to the base of transistor T2, causing T2 to stop conducting. Pin 2 of timer 88 is prevented from triggering. As transistor T2 stops conducting, capacitor C8 charges up. When capacitor C8 charges up to the threshold level of pin 6 of timer 88, the output pin 3 of timer 88 goes false. A false output on pin 3 of timer 88 energizes the alarm circuit 100 so that an audible signal is produced by the piezo element 96 in a conventional manner. False signals applied to both input terminals of NOR 86 result in a true output signal at point 104. The true signal at point 104 energizes the LED 94 to indicate an apneic event.

The true signal at point 104 is also applied to the input terminal 80b of NOR 80. Since the output signal of NAND 72 applied to terminal 80a of NOR 80 is false, the output terminal of NOR 80 goes false. The transition from true to false at pin 6 of the timer 88 causes a pulse of gas to be supplied to the in vivo respiratory system in the manner described above. If no further attempted inspiration is sensed, sequential pulses of gas are supplied in the same manner.

From the foregoing it should be apparent that a timer 90 provides a maximum time interval, and that the in vivo respiratory system must attempt a further inspiration before the expiration of the maximum time interval. If the maximum time interval is exceeded by the lapse of time from a next preceeding application of a pulse of gas to a sensing of negative pressure, the timer 90 functions to activate both the audible alarm of circuit 100 and the visible alarm of LED 94, as well as to trigger timer 90 so that a further pulse of gas is provided. The duration of the maximum time interval depends on the particular valve of the resistance Ra, Rb, Rc, . . . manually chosen by the switch 100. This resistance valve determining the rate at which capacitor C8 charges, which in turn determines the time at which the threshold voltage applied to pin 60 of the timer 88 is sufficiently high for the output state of pin 3 thereof to change.

The apparatus of the embodiment of FIG. 8A somewhat resembles the apparatus of the embodiment of FIG. 1C, but the apparatus of FIG. 8 has its sensor 28C' adapted for compatibility with an apnea detection and occlusion prevention (ADOP) circuit 200. The ADOP circuit 200 is a predominately fluidically operated circuit comprising a first fluidic timing circuit 202; a fluidic NOR gate 204; a second fluidic timing circuit 206; and, valve means 208.

The sensor circuit 28C' resembles the circuit 28 of FIG. 5 with two exceptions: (1) point 104 intermediate LED 94 and NOR 86 is not tied to the input terminal 80b of NOR 8, and (2) the output port 30c of fluidic amplifier 30 is connected by a line 210 to a point 212 in the first timing circuit 202.

Point 212 of the timing circuit 202 is connected by parallel lines 214 and 216 to a point 218. Intermediate points 218 and 212, line 214 has a fluid resistance 220 thereon while line 216 has an exhaust means, such as a mushroom valve 222, thereon. The mushroom exhaust valve 222 is oriented so that a fluid signal from point 212 is transmitted to point 218, and a fluid signal from point 212 to the valve 222 prevents point 218 from rapidly exhausting to atmosphere.

Point 212 of the timing circuit 202 is connected by line 224 to a first capacitance, such as variable volume elastomeric capacitance 226. Capacitance 226 is adapted to function in the manner of a comparable capacitance similarly depicted in U.S. patent application Ser. No. 210,653, filed Nov. 26, 1980 (incorporated herein by reference) but has a considerably longer potential volume for reasons seen hereinafter. Point 224 of circuit 202 is connected by line 228 of the NOR gate 204.

NOR gate 204 comprises a power stream input port 204a connected to a source 230; a control port 204b; a first output port 204c; and, a second output port 204d. Line 228 is connected to the control port 204b. A line 232 is connected from output port 204d to the second fluidic timing circuit 206. NOR gate 204 is of a type that, unless a signal is applied at port 204b to deflect output to port 204d, provides output at port 204c.

Output port 204d of NOR gate 204 is connected by lines 232 and 234 to a positive pressure input terminal of a conventional pressure-to-electric (P/E) switch 236. Switch 236 is connected by an electrical line L9 to indicator means 24d which includes, for example, one or more of the following: audible alarm means, visual alarm means, and counter means.

The second fluidic timing circuit 206 is essentially a fluid one-shot comprising a first output port 206a vented to atmosphere; a second output port 206b connected via line 240 to the valve 208; a first input port 206c connected to a source 230, a second input port 206d; and, a third input port 206e. Input port 206d is connected by line 232 to output port 204d of the NOR 204. The fluidic timing circuit 206 further comprises a substantially closed-loop fluidic path 244 which has a first end thereof communicating with port 206d and a second end thereof communicating with port 206e. The fluidic path 244 has thereon one or more timing means, such as a fluid restrictive device 246 and/or a capacitance device 248. As shown in the embodiment of FIG. 8, the restrictive device 246 is a variable resistor and the capacitance 248 is a variable capacitance, such as an elastomeric balloon. The restrictive device 246 and capacitance 248 can be interchanged with similar restrictive devices or capacitances having different values and capacitances as desired.

As mentioned above, output port 206b of the fluidic timing circuit 206 is connected via line 240 to the valve means 208. Valve 208 as shown is a two-way, two position solenoid spool valve, such as an ALCON Series A Model 7986 valve. Although any suitable conventional valve may be utilized. Valve 208 has two port 208a and 208b in its bore. Valve 208 is connected so that a positive pressure on line 240 moves the valve 208 into the position shown in FIG. 8A wherein port 208a thereof is connected to port 208b.

Port 208b of valve 208 is connected by line 250 to a point 252 on line. A fluidic resistor 254 on line 250 insures that the path of least resistance from the cannula 48 is through the line 46 and through the valve 26 rather than through line 250.

Port 208a of valve 208 is connected by a line 256 to a capacitance 258, which in turn is connected by line 260 to a flowmeter 262. Flowmeter 262 is connected by line 264 to a pressure regulator 266. Pressure regulator 266 is connected to a source 268.

The embodiment of FIG. 8B basically resembles the embodiment of FIG. 8A but does not employ the second fluidic timing circuit 206 and the valve means 208. Instead, the positive pressure port of the P/E switch 236 is directly connected to the output port 204d of NOR 204. The electrical output of the P/E switch 236 is connected a electrical line L10 through an electrical stimulation controller 274 to a conventional electromyographic electrode 270. Electrode 270 is positioned under the chin of a patient in close proximity to a hypoglossal nerve (the twelfth cranial nerve).

The operation of the apparatus of the embodiment of FIG. 8A basically resembles the operation of the embodiment of FIG. 1C. However, with the controller 32' of FIG. 8C, when the timer 88 of controller 32' determines that the in vivo respiratory system has not attempted a further inspiration before the expiration of a first maximum time interval, timer 90 is not triggered to provide a further pulse of gas. Moreover, although a short apnea event corresponding to the first maximum time interval has already occurred and been indicated by LED 94 and alarm circuit 100, the embodiment of FIG. 8C further functions to (1) determine when the in vivo respiratory system as failed to attempt a further inspiration before the inspiration of a second maximum time interval (the second maximum time interval being greater than the first maximum time interval and indicative of a long apnea event), and (2) to provide a high pressure pulse of gas to the in vivo respiratory system in an attempt to dislodge any occlusion or obstruction in the upper airway passages of the in vivo respiratory system.

In the above regard, when output indicative of nonnegative pressure in the in vivo respiratory system occurs at port 30e of amplifier 30, the output is applied to the first fluidic timing circuit 202. The fluidic output signal travels around line 216 of circuit 202, closing the mushroom valve 222. From thence the signal is applied to the variable capacitance 226 on line 224. The fluid signal is continuously applied to the variable capacitance device 226 so long as output occurs at port 30e of amplifier 30.

In normal breathing the output of amplifier 30 will switch to port 30d long before the variable capacitance device 226 is filled to its maximum capacity. In this regard, it is recalled that amplifier 30 switches its output from port 30e to port 30d when an inspiration is sensed. In this case, the patient is breathing satisfactorily and there is no apneic event.

In abnormal breathing, however, when the patient fails to inspire, amplifier 30 continues to generate a fluid signal on output port 30e. Accordingly, the variable capacitance device 226 continues to expand until it is inflated to its maximum capacity. When the variable capacitance device 226 is inflated to a pressure which expands it to its maximum capacity, the fluid pressure builds on line 228 and causes the power stream entering port 204a of NOR gate 204 to switch from output port 204c to output port 204d. In this manner, the NOR gate 204 creates a fluid signal on line 232. The fluid signal on lines 232 and 234 are connected to the pressure/electric switch 236 which converts the fluid signal on line 234 to an electric signal on line L9. The electric signal can perform various diagnostic operations, such as activate an electrocardiogram (ECG) monitor, an alarm, or a counter.

Various sizes and types of elastomeric balloons or other appropriate devices may be chosen for the variable capacitance device 226. Factors to be considered in making the choice of which device to use include the elastomeric tension exerted by the device and the maximum fluid-storing capacity of the device. For example, if it were desired that the apneic event circuit 200 indicate that the patient has not inspired within a 60 second-second maximum time interval, the device 226 should be selected so that it can accommodate the volume of fluid generated by amplifier 30 for that 60 second period without triggering a switch in NOR gate 204. Of course, should the patient inspire before the variable capacitance device 226 reaches its maximum pressurized capacity, the device 226 acting in conjunction with the mushroom valve 222 is quickly deflated in the manner described above.

It should be evident from FIG. 8A that, absent a fluid signal on line 232, the power stream entering port 206c of the circuit 206 is vented to atmosphere through output port 206a. However, when the fluid signal is applied on line 206d, the power stream entering at port 206c is deflected to the output port 206b for a period of time in the manner hereinafter described.

Upon application of the fluid signal on line 232 to the port 206d of the second circuit 206, the power stream entering port 206c is deflected from the output port 206a to the output port 206b, thereby creating a fluid signal on line 240 which is applied to the valve means 208. The fluid signal on line 232 is also applied to the fluidic path 244 which has thereon timing means (such as the resistance 246 and the capacitance device 248). The timing means delays the passage of the first fluid signal around the closed loop fluidic path 244 for a pre-determined time. That is, an appropriate value is chosen for the resistance of the variable resistor 246 and a capacitance device 248 of appropriate maximum capacity is chosen so that the first fluid signal travelling around the closed loop fluidic circuit 244 will be delayed for a predetermined time before the signal reaches the port 206e of the fluidic circuit 206. When the fluid signal travelling around the closed loop fluidic path 244 reaches the port 206e, the fluidic pressure on each side of the power stream entering at port 206c is equalized so that the power stream is no longer deflected out the port 206b but instead is again vented to atmosphere through the port 206a.

The valve 208 receives a supply of gas ultimately from source 268 but can transmit the gas only when a fluidic signal is applied on line 240 in the manner described above. When a fluidic signal is applied on line 240, the valve 208 is operated to connect port 208a thereof to port 208b for a time period whose duration is determined by the duration of the signal on line 240. As seen above, this duration of the signal on line 240 is determined by the selected values associated with the resistance and capacitance of the delay loop 244.

Valve 208 functions to provide a high pressure pulse of gas through line 250 to the single hose cannula 48 in an effort to dislodge an upper airway obstruction or occlusion which may have caused the long apnea event. In some instance the pressure supplied by the pulse should be as high as 50 pounds per square inch. The amplitude of the pulse is controllable through the various devices (regulator 266, capacitance 258, flowmeter 262) shown connected intermediate valve 208 and source 268.

It should be understood that various methods can be used to operate the apparatus of FIG. 8A. For example, in one mode of operation a high pressure pulse of limited duration is applied. In another embodiment the fluid circuit 206 can be adapted so that a high pressure pulse trails off to a continuous flow of lesser pressure. It can yet be envisioned that a series of high pressure pulses can be applied in a programmable manner.

The embodiment of FIG. 8B functions much in the manner of FIG. 8A but, rather than supply a high pressure pulse of gas through a valve means, uses the P/E switch 236 to generate an electrical signal on line L10 for application to the electrode 270. Electrode 270, positioned under the chin in close proximity to a nerve controlling a muscle or the like, such as the hypoglossal nerve for the tongue, provides stimulus for the muscle to dislodge itself from the upper airway so that the movement of the muscle and associated organs can again be in coordination with the diaphragm of the in vivo respiratory system.

FIG. 8C illustrates a further embodiment of the invention which accomplishes objectives similar to that of the embodiment of FIG. 8A. The apparatus of FIG. 8C resembles the apparatus of FIG. 6. The controller 32' of FIG. 8C, however, does not have its point 104 connected to the input terminal 80b of NOR 80. Rather, point 104 is connected by line L7 to a two-position two port solenoid spool valve 272. Valve 272 of FIG. 8C is connected to a source 268 in much the same manner as valve 208 of FIG. 8A is connected to source 268.

In the operation of the embodiment of FIG. 8C, whenever controller 32' determines that an apnea event [having a duration corresponding to a predetermined yet variably selectable maximum time interval established by the position of switch 100] occurs, a high pressure pulse of gas is supplied through the operation of valve 272 in a manner easily understood from the foregoing other embodiments.

It should be understood that sensing means 28C of the embodiment of FIG. 1C may be used with any of the embodiments disclosed herein. Also, each of the disclosed embodiments may be appropriately modified as discussed above to operate in either a spiked pulse or a square pulse mode. Further, it should be understood by those skilled in the art that the solenoid operated spool valves disclosed herein may be replaced with latching solenoid valves, such as the Neutronics Series 11 valve.

The embodiments of the invention in which an exclusive property or privilege is claimed are defined as follows:

1. An apparatus for sensing, negative pressure indicative of inspiration in an in vivo respiratory system and for supplying gas to said in vivo respiratory system, said apparatus comprising:
 means for sensing negative pressure in said in vivo system;
 valve means operable for selectively supplying said gas to said in vivo system;
 control means responsive to said sensing means for operating said valve means whereby said gas is supplied to said in vivo system for at least a portion of the time duration of an occurrence of sensed negative pressure;
 first timer means connected to said sensing means for determining when a first predetermined time interval has elapsed since the last occurrence of negative pressure in said in vivo system; and,
 means responsive to said first timer means for stimulating a nerve associated with upper airway in vivo neuro-muscular tissue that will displace said tissue when stimulated whereby an upper airway passage in said in vivo respiratory system is not occluded, said stimulation occurring upon the elapse of said predetermined time interval.

2. The apparatus of claim 1, wherein said in vivo tissue is a tongue.

3. The apparatus of claim 2, wherein said in vivo tissue comprises pharyngeal muscles.

4. The apparatus of claim 1 further comprising second timer means connected to said sensing means for determining when a second predetermined time interval less than said first predetermined time interval has elapsed since the last occurrence of negative pressure in said in vivo system without a further occurrence of negative pressure in said in vivo system; and,
 counter means for counting the number of events wherein the time interval between successive occurrences of negative pressure in said in vivo system is greater than said second predetermined time interval.

5. The apparatus of claim 1, wherein said airway is the oropharyngeal airway.

6. The apparatus of claim 1, wherein said nerve is the hypoglossal nerve.

7. A method for supplying gas to an in vivo respiratory system and for monitoring the condition of said in vivo respiratory system, said method comprising the steps of:
 sensing negative pressure in said in vivo respiratory system;
 using valve means to selectively supply gas to said in vivo system;
 controlling the operation of said valve means whereby gas is supplied to said in vivo system for at least a portion of the time duration of an occurrence of sensed negative pressure;

determining when a first predetermined time interval has elapsed since the last occurrence of negative pressure in said in vivo system; and, stimulating a nerve associated with upper airway in vivo neuro-muscular tissue that will displace said tissue when stimulated whereby an upper airway passage in said in vivo respiratory system is not occluded, said stimulation occurring upon the elapse of said first predetermined time interval.

8. The method of claim 7, wherein said in vivo organ is a tongue.

9. The method of claim 7, wherein said in vivo organ comprises pharyngeal muscles.

10. The apparatus of claim 7, wherein said airway is the oropharyngeal airway.

11. The apparatus of claim 7, wherein said nerve is the hypoglossal nerve.

12. An apparatus for detecting an apnea event in an in vivo respiratory system and for removing an upper airway obstruction associated with an obstructive apnea event, said apparatus comprising:

means for sensing negative pressure in said in vivo system;

first timer means connected to said sensing means for determining when a predetermined time interval has elapsed since the last occurrence of negative pressure in said in vivo system; and, means responsive to said first timer means for simulating a nerve associated with upper airway neuro-muscular tissue that will displace said tissue when stimulated to dislodge an occlusion of an upper airway passage in said in vivo respiratory system, said stimulation occurring upon the detection of the elapse of said predetermined time interval.

13. The apparatus of claim 12, wherein said in vivo tissue is a tongue.

14. The apparatus of claim 12, wherein said in vivo tissue comprises pharyngeal muscles.

15. The apparatus of claim 12, wherein said airway is the oropharyngeal airway.

16. The apparatus of claim 12, wherein said nerve is the hypoglossal nerve.

17. A method of detecting an apnea event in an in vivo respiratory system and of removing an upper airway obstruction associated with an obstructive apena event, said method comprising the steps of:

sensing negative pressure in said in vivo respiratory system;

determining when a predetermined time interval has elapsed since the last occurrence of negative pressure in said in vivo system; and, stimulating a nerve associated with upper airway neuro-muscular tissue that will displace said tissue when stimulated to dislodge an occlusion of an upper airway passage in said vido respiratory system, said stimulation occurring upon the elapse of said first predetermined time interval.

18. The method of claim 1, wherein said in vivo tissue is a tongue.

19. The method of claim 17, wherein said in vivo tissue comprises pharyngeal muscles.

20. The apparatus of claim 17, wherein said airway is the oropharyngeal airway.

21. The apparatus of claim 17, wherein said nerve is the hypoglossal nerve.

* * * * *